United States Patent [19]

Nakao et al.

[11] 4,356,172

[45] Oct. 26, 1982

[54] ERYTHROCYTE PRESERVATIVE AND BLOOD PRODUCTS FOR LONG-TERM STORAGE

[75] Inventors: Makoto Nakao; Toshiko Nakao; Fumiko Nagai; Masako Dogen, all of Tokyo; Yoshitomi Tabata, Kamakura, all of Japan

[73] Assignee: Kuraray Co., Ltd., Kurashiki, Japan

[21] Appl. No.: 178,438

[22] Filed: Aug. 15, 1980

[30] Foreign Application Priority Data

Mar. 31, 1980 [JP] Japan .................................. 55-42623

[51] Int. Cl.$^3$ ............................................. A61K 35/14
[52] U.S. Cl. ........................................ 424/101; 435/2
[58] Field of Search ............................. 435/2; 424/101

[56] References Cited

U.S. PATENT DOCUMENTS 4,267,269 5/1981 Grode et al. ............................ 435/2

OTHER PUBLICATIONS

Chan et al., Chem. Abst. vol. 82 (1975), p. 95979f.
Meryman, Chem. Abst. vol. 79, (1973). p. 112107c.
Seidl, Chem. Abst. vol. 77, (1972), p. 3321f.
Dawson et al., Chem. Abst. vol. 81, (1974), p. 117893g.
Strumia et al., Chem. Abst. vol. 77, (1972) p. 46221r.
Fujii et al., Chem. Abst. vol. 80, (1974), p. 57932m.
Benes et al., Chem. Abst. vol. 84, (1976), p. 119269u.

Primary Examiner—Sam Rosen
Attorney, Agent, or Firm—Barry Kramer

[57] ABSTRACT

An erythrocyte preservative is provided which contains an erythrocyte membrane strengthening agent, optionally a purine base and/or purine nucleoside and optionally an anticoagulant. Blood products which contain the above erythrocyte preservative and can be stored for a prolonged period of time are also provided.

4 Claims, No Drawings

ERYTHROCYTE PRESERVATIVE AND BLOOD PRODUCTS FOR LONG-TERM STORAGE

BACKGROUND OF THE INVENTION

1. Field of the Invention

This invention relates to an erythorocyte (red blood cell) preservative and an erythrocyte preparation storable for a prolonged period of time.

2. Description of the Prior Art

With recent advances in medical technology, the demand for blood for transfusion is increasing steadily. (In this specification, the term "blood" includes not only the whole blood but also red cell suspensions, packed red cell or erythrocyte concentrates and other blood component preparations containing erythrocytes.) However, the blood cannot be used later than 3 weeks after it has been drawn, even if stored at 4° C., and therefore the blood is not used very efficiently but its supply is always tight. One obvious reason is that erythrocytes deteriorate during storage and the deterioration shortens the life time of erythrocytes after transfusion. Therefore, studies have been made with the object of prolonging the life of ertyhrocytes by adding substances involved in the metabolism of erythrocytes to the blood to be stored. In particular, Makoto Nakao and Toshiko Nakao [Journal of the Japanese Medical Association 75 (1), 15-28 (1976)] have found that addition of adenine in concentrations of 2 to 10 mM and of inosine in concentrations of 5 to 50 mM, each as a substance required for the metabolism of erythrocytes, can extend the allowable period of blood storage to nearly 8 weeks. This finding opened the way to efficient use of blood.

However, since excessive amounts of adenine, inosine, substances related thereto which are contained therein, and further metabolites thereof, supposedly give rise to the formation of harmful substances such as uric acid in the body, it is necessary to remove these substances prior to the practical use of the stored blood in transfusion. Conventionally, removal is effected by washing erythrocytes with an isotonic aqueous solution such as physiological saline and, preferably, removing the substances in question by adsorption using such an adsorbent as activated carbon coated with a blood-compatible layer. Unfortunately, the present inventors have found that such procedures, when applied to stored erythrocytes, often lead to hemolysis. While hemolysis can be prevented to a considerable extent by addition of adenine and inosine as compared with the case where neither adenine nor inosine is added, it is still necessary to further increase the hemolytic resistance of erythrocytes.

SUMMARY OF THE INVENTION

The present inventors, as a result of intensive investigation of this problem, have now found that the erythrocyte membrane is strengthened or reinforced by addition of a specific group of compounds to erythrocyte pereparations, whereby hemolysis is prevented. The present invention is based on this finding.

Thus, the invention provides an erythrocyte preservative which contains an erythrocyte membrane strengthening agent and further, blood products storable for a prolonged period of time which comprise erythrocytes and said erythrocyte preservative in sufficient amount to establish isotonicity between the inside and outside of the erythrocyte membrane.

DETAILED DESCRIPTION OF THE INVENTION

The erythrocyte membrane strengthening agent to be used in the practice of the present invention is a water-soluble substance to which the erythrocyte membrane is nonpermeable. Naturally for the purposes of the invention, the agent must be harmless and stable against sterilization. The erythrocyte membrane strengthening agent is a compound selected from the group consisting of disaccharides, reduced derivatives thereof, polyhydric alcohols containing at least 4 hydroxyl groups, and mixtures of these. Typical examples are sucrose, lactose, maltose, maltitol, sorbitol and mannitol. Polybasic or polyfunctional carboxylate salts such as succinates, malonates and oxalates also may act as the erythrocyte membrane strengthening agents but are not so effective as the ones mentioned above; they are not favorable from the toxicological standpoint, hence they are not suited for practical uses.

The concentration of the erythrocyte membrane strengthening agent in the preservative is preferably in the range of 10 to 500 millimoles per liter. At lower concentrations, no substantial effect can be expected; whereas, at higher concentrations, the filtrability of blood is reduced and further the hemolytic resistance rather shows a tendency toward reduction. When sucrose is used, its concentration is preferably 50 to 500 millimoles per liter, especially 100 to 400 millimoles per liter. Such pereservative is added to an erythrocyte fraction separated from the whole blood so as to establish isotonicity between the inside and the outside of the erythrocyte. In the prior art, it is also known to establish isotonicity between the inside and outside of the erythrocyte in erythrocyte preparations by merely adding such an electrolyte as a citrate or phosphate, or glucose. In such prior art techniques, it is anticipated that the electrolyte or glucose and metabolites thereof, which can freely permeate through the erythrocyte membrane, will cause delicate changes in intracellular components, which changes may adversely affect storability of the erythrocyte. On the contrary, the erythrocyte preservative of the present invention, being incapable of permeating through the erythrocyte membrane, will not affect the intracellular components but can prevent erythrocytes from degeneration or deterioration. Such findings and such effects are characteristic features of the present invention.

The invention also provides an improved erythrocyte preservative which contains a purine base and/or a purine nucleoside together with the erythrocyte membrane strengthening agent mentioned above. The present invention further provides another improved erythrocyte preservative which contains an anticoagulant as well as a purine base and/or a purine nucleoside together with the erythrocyte membrane strengthening agent.

Purine bases and purine nucleosides are substances necessary in the metabolic cycle for etythrocytes. It has been found that addition of these substances to blood to be stored can maintain increased levels of adenosine triphosphate (ATP) and 2,3-diphosphoglycerate (2,3-DPG) and can prolong the life of erythrocytes after transfusion and thereby further improve the storability of erythrocyte preparations.

Addition of at least one of the purine base and purine nucleoside will suffice. Typical examples are adenine and inosine. Preferably, the erythrocyte preservative contains adenine in a concentration of 2 to 10 millimoles per liter and inosine in a concentration of 5 to 50 millimoles per liter. The preservative which contains the erythrocyte membrane strengthening agent and the purine base and/or purine nucleoside can prolong the period during which erythrocytes can be stored without degeneration, prevent hemolysis at the time of transfusion and moreover, prolong the life of erythrocytes after transfusion.

In accordance with a preferred feature of the invention, the preservative of the invention may also contain citric acid or a salt thereof, which is known as an anticoagulant. The concentration of citric acid is preferably 1 to 20 millimoles per liter, and, in the case of sodium citrate, its concentration is preferably 10 to 100 millimoles per liter. The preservative may further contain glucose as an energy source for erythrocytes and/or such a salt as a phosphate, if desired.

The preservative of the invention placed in the form of an aqueous solution in a closed container for storing blood can, in accordance with the practice in the art, be sterilized by an appropriate method such as thermal sterilization or irradiation. After the sterilization, the preservative can aseptically be mixed with whole blood just drawn or a blood preparation containing erythrocytes, such as an erythrocyte suspension, to make a blood product containing erythrocytes for transfusion, which can be preserved at 4° C. for a longer period than in the case of conventional formulations. Thus, for example, the erythrocyte product can be used for transfusion even after storage for more than 8 weeks.

The erythrocyte preservative of the present invention should be added to erythrocytes or erythrocyte preparations in a sufficient amount to establish isotonicity between the inside and outside of the erythrocyte. Since the erythrocytes or erythrocyte products may have a wide range of concentrations depending upon the conditions of preparing the same, it is not easy to strictly and explicitly specify the amount of the preservative to be added. Preferably, however, the volume ratio of the preservative to erythrocytes in the erythrocyte preparations of the present invention is within the range of 1:10 to 10:1.

Naturally, the erythrocyte preservative of the present invention can be added not only to human erythrocytes but also erythrocytes of warm-blooded animals other than humans. The erythrocyte product for transfusion is subjected, prior to infusion into an organism, to the above-mentioned treatment for removal of undesirable substances to the organism, such as washing with isotonic physiological saline or, more preferably, treatment with an adsorbent having a blood-compatible coating thereon.

The following examples will illustrate the invention in more detail. These examples are for illustrative purposes only and are not to be construed as imposing any limitations on the spirit or scope of the present invention. Unless otherwise stated, all percentages and parts are by weight.

EXAMPLE 1

A human erythrocyte concentrate having a hematocrit value of 65 to 75% was added to a solution of an erythrocyte membrane strengthening agent in a 0.9% aqueous sodium chloride solution, and, after incubation, the erythrocytes were added to a 0.3% or 0.45% aqueous sodium chloride solution and observed for hemolysis. The results are shown in Table 1 and in Table 2.

TABLE 1

| Hemolysis inhibiting effects of saccharides and polyhydric alcohols | | |
|---|---|---|
| Additive (concentration) | | Conditions of incubation Hemolysis (in 0.3% sodium chloride) 37° C., 3 hours |
| None | | 88.0% |
| Sucrose | (300mM) | 8.4 |
| Lactose | " | 7.0 |
| Mannitol | " | 11.9 |
| Glucose | " | 95.0 |
| Glycerol | " | 97.8 |

TABLE 2

| Hemolysis inhibiting effects of dibasic carboxylic acids | | | |
|---|---|---|---|
| | | Conditions of incubation Hemolysis (in 0.45% sodium Chloride) | |
| Additive (concentration) | | Room temperature 30 minutes | 4° C., 24 hours |
| None | | 71.4% | 71.3% |
| Oxalic acid | (50 mM) | 35.7 | 44.2 |
| Succinic acid | " | 32.1 | 31.4 |
| Malonic acid | " | 32.0 | 27.1 |

It is evident from the above results that, while the dibasic acids are also effective in inhibiting hemolysis to a certain extent, sucrose and lactose are very effective, then follows mannitol, but glucose and glycerol are not effective at all.

EXAMPLE 2

Human packed red cells (hereinafter "PC") with a hematocrit value of 65 to 75% were used. Two preservative solutions were prepared, namely Solution A (2 mM citric acid, 10 mM sodium citrate, 4 mM disodium hydrogenphosphate, 15 mM glucose and 250 mM sucrose) and Solution B (Solution A plus 8 mM adenine and 40 mM inosine). 7.7 ml of each preservative solution was added to 10 ml of PC and the mixture was stored at 4° C. under aseptic conditions. The 50% hemolytic values after 15 to 81 days of storage are shown in Table 3. The 50% hemolytic value is the concentration of the aqueous sodium chloride solution which causes hemolysis of 50% of erythrocytes. The smaller the hemolytic value, the greater is the resistance to hemolysis.

TABLE 3

| 50% Hemolysis values (sodium chloride concentrations) for preserved erythrocytes | | | | |
|---|---|---|---|---|
| Preservative solution | Storage period | | | |
| | 15 days | 26 days | 45 days | 81 days |
| PC | 0.46% | 0.45 | 0.54 | — |
| Solution A | 0.35 | 0.27 | 0.23 | — |
| Solution B | 0.23 | 0.21 | 0.20 | 0.16 |

The above results indicate that the hemolytic resistance of preserved erythrocytes is increased by the addition of sucrose to the preservative solution and still further increased by the addition of adenine and inosine.

EXAMPLE 3

Blood was drawn from JW/KBL strain rabbits. Three preservative solutions were prepared, namely CPD solution (15 mM citric acid, 87 mM sodium citrate, 15 mM disodium hydrogenphosphate and 139 mM glucose), Solution A' (8 mM citric acid, 40 mM sodium citrate, 8 mM disodium hydrogenphosphate, 30 mM glucose and 250 mM sucrose) and Solution B' (Solution A' plus 8 mM adenine and 40 mM inosine). The CPD solution was added to the blood in a ratio of 450:63, and Solution A' and Solution B' were each added to the blood in equal amounts. The mixtures were preserved at 4° C. for 5 weeks under aseptic conditions.

The blood samples preserved in the above manner and fresh rabbit blood were assayed for 2,3-DPG content enzymochemically and for ATP content by high-speed liquid chromatography. Separately, about 10μ Ci of $^{51}$Cr-labelled sodium chromate was added to 5 ml of each preserved blood sample for labelling erythrocytes and an erythrocyte suspension with a hematocrit value of 50% was prepared. 1.0 to 1.5 ml of the erythrocyte suspension was injected intravenously into the same rabbits from which the blood had been drawn. Five minutes later and 24 hours later, respectively, blood samples were drawn and assayed for erythrocyte survival percentages. The results of these assays are shown in Table 4.

TABLE 4

Rabbit blood ATP and 2,3-DPG contents and erythrocyte survival percentages 24 hours after transfusion

| Preservation conditions | ATP content μmoles/g hemoglobin | 2,3-DPG content μmoles/g hemoglobin | Percent erythrocyte survival* |
|---|---|---|---|
| Fresh blood | 5.39 | 26.4 | 106.1% |
| CPD solution, 5 weeks | 0.42 | 8.0 | 28.5 |
| Solution A', 5 weeks | 0.77 | 6.2 | 59.5 |
| Solution B', 5 weeks | 3.52 | 24.3 | 84.5 |

*The count 5 minutes after transfusion = 100

The above results indicate that the ATP and 2,3-DPG contents in the preserved blood can be maintained at levels almost equal to those in the fresh blood by the supplemental addition of adenine and inosine and that the erythrocyte survival percentage after transfusion can be doubled by the addition of sucrose as compared with the conventional formulation and tripled by the addition of sucrose, adenine and inosine.

What is claimed is:

1. A blood product for long-term storage which comprises erythrocytes and an erythrocyte preservative containing effective amounts of a disaccharide as an erythrocyte membrane strengthening agent, adenine, inosine, and a anti-coagulant.
2. A blood product according to claim 1 wherein the disaccharide is sucrose or lactose.
3. A Blood product according to claim 1 wherein the anti-coagulant is citric acid or a salt thereof.
4. The blood product according to claims 2 or 1 in which the concentration ratio of the (erythrocyte membrane strengthening agent)/(adenine)/(inosine)/(anti-coagulant) is 10-500/2-10/5-50/1-100.